United States Patent [19]

Romaine

[11] 4,270,537
[45] Jun. 2, 1981

[54] AUTOMATIC HYPODERMIC SYRINGE

[76] Inventor: Richard A. Romaine, 475 SW. View Crest Dr., Gresham, Oreg. 97030

[21] Appl. No.: 95,402

[22] Filed: Nov. 19, 1979

[51] Int. Cl.³ ............................................. A61M 5/00
[52] U.S. Cl. .............................. 128/218 A; 128/218 F
[58] Field of Search ............... 128/218 F, 218 A, 215, 128/216

[56] References Cited

U.S. PATENT DOCUMENTS

| | | | |
|---|---|---|---|
| 3,073,306 | 1/1963 | Linder | 128/215 |
| 3,605,742 | 9/1971 | Tibbs | 128/218 F |
| 3,702,608 | 11/1972 | Tibbs | 128/218 F |
| 4,085,748 | 4/1978 | Boyer | 128/218 F |

Primary Examiner—John D. Yasko
Attorney, Agent, or Firm—Eugene D. Farley

[57] ABSTRACT

A hypodermic syringe and automatic needle insertion device wherein the syringe is biased against a trigger when the needle is in its retracted position. Upon release of the trigger the syringe and needle are driven forward, extending the needle into the underlying tissue. The depth of insertion may be predetermined by the attachment of an interchangeable stop or foot extension.

7 Claims, 6 Drawing Figures

AUTOMATIC HYPODERMIC SYRINGE

BACKGROUND OF THE INVENTION

This invention relates to an automatic needle insertion device in conjunction with a hypodermic syringe, in which the device is held against the patient at the location where the injection is to be made and, upon release of a trigger the needle is driven into the underlying tissue to a predetermined depth.

Automatic hypodermic syringes of the class of the present invention are well known in the art (U.S. Pat. Nos. 2,671,448 and 2,856,924). While such automatic syringes are useful for their intended purpose, they are complicated in design and operation, and require a syringe or ampoule of unconventional or specific design, and a needle of specific length.

There is need for a simply constructed and easily operated device, capable of being used with conventional syringes of various sizes and having various needle lengths, which will quickly and painlessly insert the needle into the patient. One of the uses of such a device is in the self-administration of medication by persons such as diabetics, highly allergic individuals who must use injectable drugs, or by military personnel where unskilled first-aid must be administered.

It is important in such a device that the contents of the syringe be viewable and the plunger be unencumbered, so that when the needle has been inserted into the underlying tissue the syringe may be aspirated to observe for blood and consequently determine that the needle has not penetrated a blood vessel. It is also important to maintain the syringe immobile during the injection, thereby reducing pain.

The experience of receiving a hypodermic injection should be a relatively painless one. By accomplishing this children and adults will have less apprehension for future injections. The greater the speed of a hypodermic needle penetration into the skin, the less the pain will be perceived. Further, in order to reduce anxiety and fear, the needle should be hidden. This is especially important when approaching children who are to receive an injection. In the case of self injection, it should not be necessary to plunge the needle manually into the skin.

Accordingly, it is the general object of this invention to provide a hypodermic syringe assembly which is automatic in its insertion of the needle into the underlying tissue.

It is another object of this invention to provide a device which is easily adaptable to various size syringes and needle lengths.

It is a further object of this invention to provide a syringe having a window through which the contents of the syringe may be viewed.

It is a further object of this invention to provide a substantial base which may be placed directly against the skin to hold the syringe immobile throughout the duration of the injection.

It is a further object of this invention to provide a syringe wherein the insertion of the needle into the underlying tissue is substantially instantaneous.

It is a further object of this invention to provide a syringe wherein the needle is not visible prior to use.

It is a further object of this invention to provide a syringe wherein the needle does not have to be manually plunged into the skin.

DRAWINGS

The manner in which the foregoing and other objects of the invention are accomplished will be apparent from the accompanying specification and claims, considered together with the drawings, wherein:

GENERAL STATEMENT OF THE INVENTION

The automatic hypodermic syringe of the present invention generally comprises a conventional syringe in combination with an insertion mounting therefor. The mounting comprises a hollow cylinder in which the syringe may be longitudinally inserted, a trip which releasably supports the syringe in the cylinder, a resilient drive means biasing the syringe against the trigger, and a means for limiting the depth of penetration of the needle. Upon release of the trip, the syringe and needle are driven forward, extending the needle into the underlying tissue.

DETAILED DESCRIPTION OF THE PREFERRED EMBODIMENTS

Figure 1:
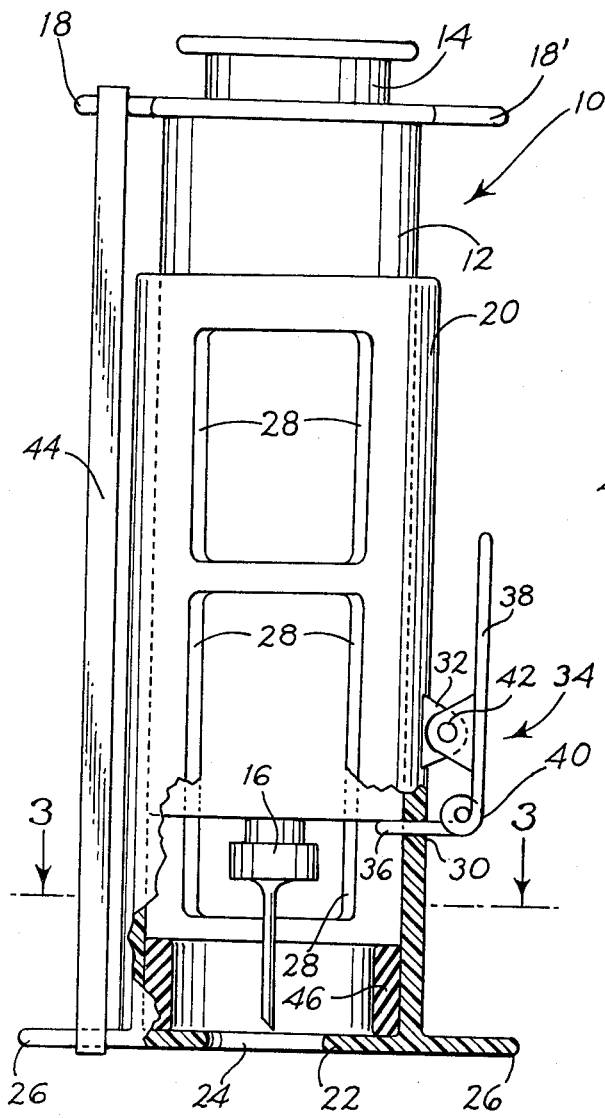
FIG. 1 is generally, an elevation of the syringe and insertion device with the bottom part thereof broken away to show the internal construction, the trigger being engaged and the needle in its retracted position, and a means of limiting the depth of penetration of the needle, in a first embodiment.
Figure 2:
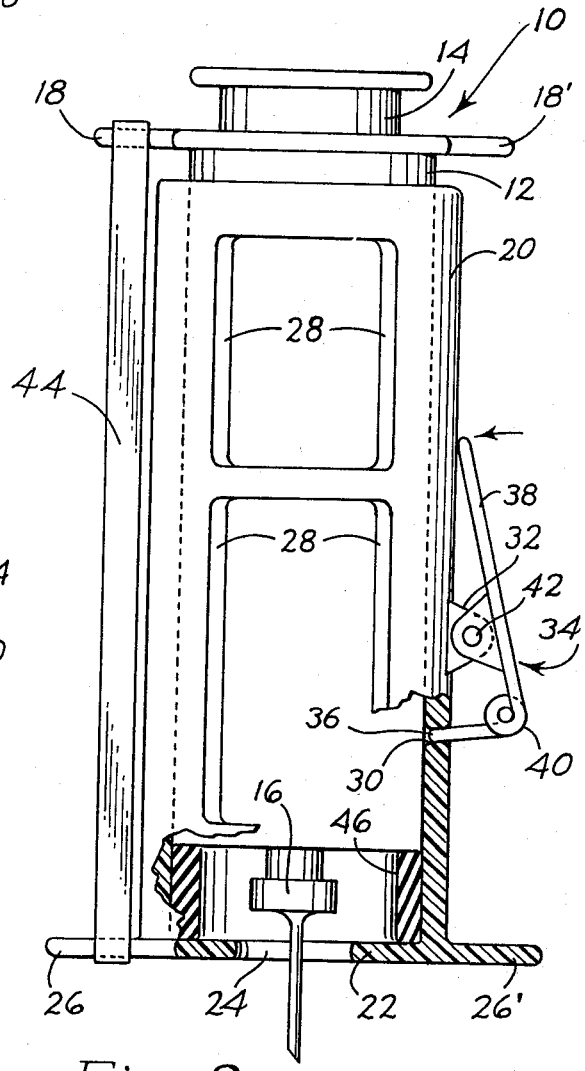
FIG. 2 is a view similar to FIG. 1, showing the trigger released, and the needle in its extended position.
Figure 3:
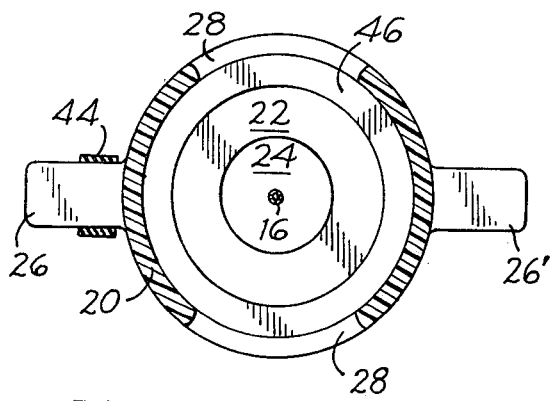
FIG. 3 is a section on the line 3—3 of FIG. 1.

FIGS. 1 and 2 show the automatic hypodermic syringe of the present invention, the bottom part thereof shown broken away exposing the internal construction. Syringe 10 is of conventional design, having barrel 12, plunger 14 longitudinally reciprocateable within barrel 12 and hypodermic needle 16 attached to the bottom end of barrel 12.

Flanges 18 and 18' extend outwardly from the top of barrel 12. Barrel 12 is normally transparent, allowing visual inspection of the syringe contents. Needle 16 may be of varying length. The features of the present invention which compensate for such variation will be discussed hereinafter.

Syringe 10 is contained in a hollow cylinder 20 dimensioned to receive barrel 12 of the syringe in a longitudinal sliding relationship. The top of cylinder 20 is open, and the bottom is partially closed by base 22, which has hole 24 in the center thereof to allow passage of needle 16.

Feet 26 and 26' flange outwardly from the bottom of cylinder 20. They have a dual purpose: First, to add stability to the syringe when it is placed against the patient, and second, to provide an attachment for the drive means as is hereinafter discussed.

Cylinder 20 also includes window means 28 which provides for visual inspection of the syringe contents. The window means may be a transparent section, or a large opening in the side wall of cylinder 20. Although window means 28 should allow inspection of the syringe contents in all positions of the syringe, it will preferably not allow the needle to be readily observed.

In the side wall of cylinder 20 is located hole 30, and above hole 30 a pivot base 32 flanges from the side wall.

Releasably supporting syringe 10 within cylinder 20 is a trip means, preferably a trigger shown generally as 34. Detent 36 extends into cylinder 20 through hole 30 and supports syringe 10. Detent 36 is attached to lever 38 by hinge 40, and lever 38 is attached to pivot base 32 in a rocking relationship by pivot 42.

Barrel 12 is biased against detent 36 by a resilient drive means in the form of rubber band 44 interconnecting flange 18 and foot 26.

The depth that the needle penetrates into the underlying tissue may be limited by a stop means, the first embodiment thereof being shown in FIGS. 1 and 2 as an interchangeable abutment washer 46. Washer 46 may be placed by the user within cylinder 20, at the bottom thereof, below barrel 12.

Figure 4:
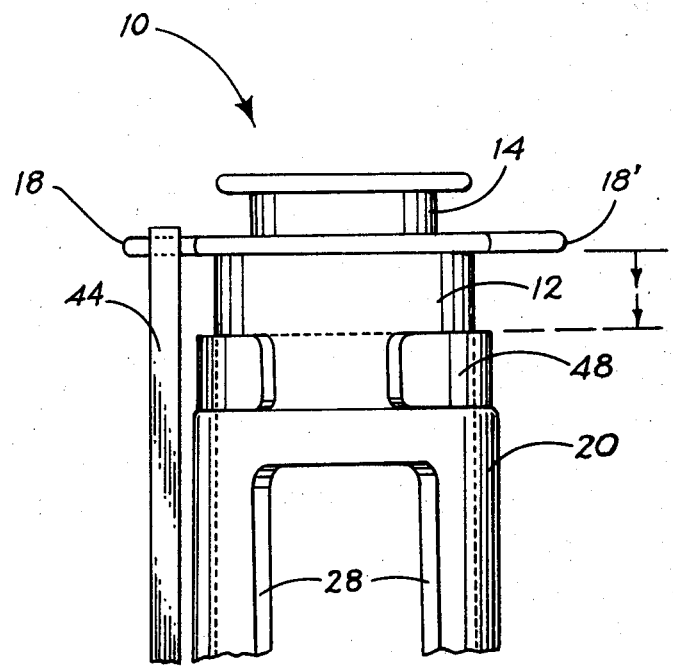
FIG. 4 is a fragmentary view similar to FIG. 1, showing the top of the syringe and means for limiting the depth of penetration of the needle, in a second embodiment.

A second embodiment of stop means and penetration limiting means is shown in FIG. 4. Interchangeable abutment collar 48 may be mounted by the user on barrel 12 above the top of cylinder 20.

Figures 5, 6:
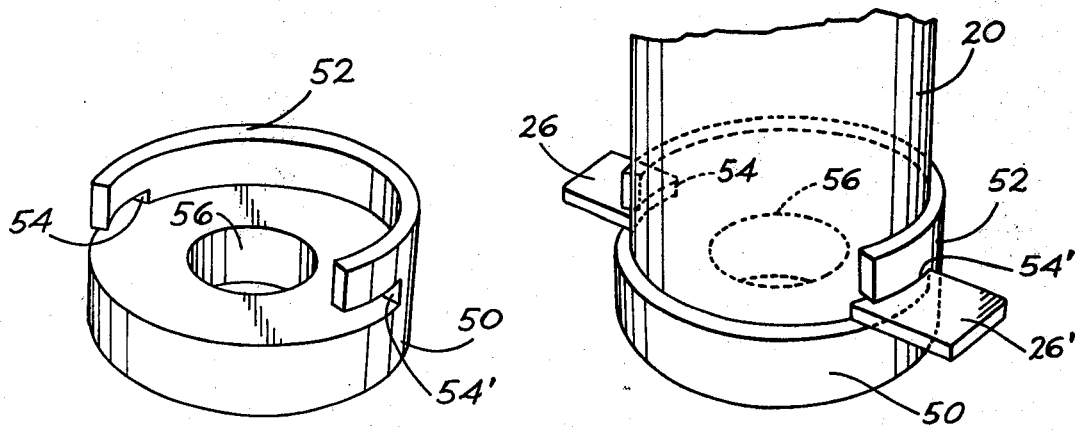
FIG. 5 is a perspective view of an attachment for limiting the depth of penetration of the needle, in a third embodiment.
FIG. 6 is a fragmentary perspective view showing the penetration limiting attachment of FIG. 5 in working position on the insertion device.

A third embodiment of a penetration limiting means is shown in FIGS. 5 and 6. Base extension 50 is an interchangeable attachment which may be attached by the user to the bottom of cylinder 20. Clip 52 snaps around the bottom exterior of cylinder 20 and a pair of recesses 54 and 54' allow the clip 52 to extend over feet 26 and 26'.

Base extension 50 is dimensioned with substantially the same cross section as the bottom of cylinder 20. It has a hole 56 therein to allow passage of needle 16.

It is preferred to have the bottom of base extension 50 in a plane which is substantially perpendicular to the longitudinal axis of cylinder 20. However, this is not necessary, and a deviation from this embodiment would allow needle 16 to penetrate the underlying tissue at an angle.

OPERATION

Syringe 10 is readied for injection in the conventional manner. Then, depending on needle length, and if needed, an appropriately sized penetration limiting means is selected and placed in position. This penetration limiting means may be abutment washer 46, abutment collar 48, or base extension 50, or a combination thereof. Trigger 34 is then engaged by moving lever 38 to insert detent 36. Syringe 10 is inserted into cylinder 20 and rubber band 44 is stretched between foot 26 and flange 18.

Next the bottom of the assembly is placed solidly against the patient at the location where the injection is to be administered. Thereupon, lever 38 is pressed, retracting detent 36, and allowing rubber band 44 to contract, driving syringe 10 forward and inserting needle 16 into the underlying tissue.

Syringe 10 is then aspirated by slightly retracting plunger 14 and an observation is made for blood through window 28. If no blood is visible in syringe 10, then it is known that needle 16 has not entered a blood vessel, and the injection may proceed normally.

Upon completion of the injection, the entire mechanism is lifted away from the patient, withdrawing needle 16.

Having thus described my invention in preferred embodiments, I claim:

1. An automatic hypodermic syringe assembly comprising, in combination:
   (a) a syringe, comprising a barrel, a reciprocating plunger within the barrel, and a needle attached to the bottom of the barrel; and
   (b) an insertion mounting therefor, the mounting comprising:
      (1) a hollow cylinder, open at the top, dimensioned to receive the syringe barrel in longitudinal sliding relationship, and having a base at the bottom with a hole therein dimensioned to pass the needle,
      (2) trip means engaging the cylinder and the syringe, operable to releasably support the syringe barrel within the cylinder,
      (3) resilient drive means interconnecting the syringe barrel and the cylinder, and operable to advance the barrel in the cylinder upon release of the trip means, thereby extending the needle, and
      (4) interchangeable penetration limiting means, operable to predetermine the maximum extension of the needle.

2. The automatic hypodermic syringe assembly of claim 1 wherein the trip means comprises a lever operated detent operable to releasably support the bottom of the syringe barrel.

3. The automatic hypodermic syringe assembly of claim 1 further comprising a syringe-stabilizing foot flanging from the bottom of the cylinder.

4. The automatic hypodermic syringe assembly of claim 1 wherein the penetration limiting means comprises an interchangeable base extension attached to and extending below the cylinder and dimensioned with substantially the same cross section as the bottom thereof.

5. The automatic hypodermic syringe assembly of claim 1 wherein:
   (a) the trip means comprises a lever-operated detent,
   (b) a stabilizing foot flanges from the bottom of the cylinder,
   (c) a flange extends outwardly from the top of the barrel,
   (d) the resilient drive means comprises a rubber band interconnecting the flange and the foot,
   (e) the penetration limiting means comprises an interchangeable base extension attached to and extending below the cylinder and dimensioned with substantially the same cross section as the bottom thereof, and including,
   (f) a window means in the cylinder providing for visual inspection of the syringe contents.

6. The automatic hypodermic syringe assembly of claim 1 wherein the penetration limiting means comprises an interchangeable abutment washer located within the cylinder, at the bottom thereof, below the syringe barrel, and operable to abut the bottom of the barrel and the base of the cylinder, thereby restricting further advancement of the syringe barrel in the cylinder.

7. The automatic hypodermic syringe assembly of claim 1 wherein the syringe further comprises a flange extending outwardly from the top of the barrel, and wherein the penetration limiting means comprises an interchangeable collar mounted on the syringe barrel above the top of the cylinder and operable to abut the flange and the top of the cylinder, thereby restricting further advancement of the syringe barrel in the cylinder.

* * * * *